United States Patent

Okada et al.

[11] Patent Number: 5,436,283
[45] Date of Patent: Jul. 25, 1995

[54] DENTURE BASE LINING MATERIAL

[75] Inventors: Junichi Okada; Yukari Nasu, both of Tokyo, Japan

[73] Assignee: GC Corporation, Tokyo, Japan

[21] Appl. No.: 210,943

[22] Filed: Mar. 21, 1994

[30] Foreign Application Priority Data

Mar. 26, 1993 [JP]  Japan .................. 5-090510

[51] Int. Cl.⁶ .................. C08K 5/12; C08L 33/10; A61K 6/083
[52] U.S. Cl. .................. 523/120; 523/109; 524/296; 524/297; 524/390; 524/490; 524/556; 524/560
[58] Field of Search ............ 523/120, 109; 524/296, 524/297, 390, 490, 556, 560

[56] References Cited

U.S. PATENT DOCUMENTS

| | | | |
|---|---|---|---|
| 2,296,877 | 9/1941 | Slack, Jr. ..................... | 523/109 |
| 4,761,136 | 8/1988 | Madhavan et al. .......... | 523/109 |
| 5,120,360 | 6/1992 | Tajiri et al. .................. | 523/161 |
| 5,256,191 | 10/1993 | Thompson et al. .......... | 106/285 |
| 5,306,755 | 4/1994 | Yau et al. ..................... | 524/430 |

*Primary Examiner*—Paul R. Michl
*Assistant Examiner*—Andrew E. C. Merriam
*Attorney, Agent, or Firm*—Oblon, Spivak, McClelland, Maier & Neustadt

[57] ABSTRACT

A denture base lining material to be used upon mixing a liquid component and a powder component is disclosed, characterized in that the liquid component comprises a phthalic ester-based plasticizer and containing from 5 to 15% by weight of ethyl alcohol and from 5 to 20% by weight of a liquid paraffin or squalane alone or a mixed solution thereof, and the powder component comprises a powder comprising any one of the following powders (a), (b), or (c), or a mixture of two or more thereof: (a) an ethyl methacrylate polymer powder containing from 1 to 5% by weight of a phthalic ester-based plasticizer; (b) a copolymer powder represented by the following formula:

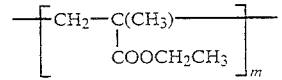

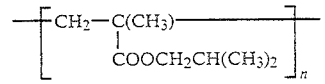

wherein $n/(m+n)$ is from 0.15 to 0.55, and containing from 0.5 to 2% by weight of a phthalic ester-based plasticizer; and (c) a mixed powder comprising a polyethyl methacrylate powder having a copolymer powder represented by the following formula mixed therewith:

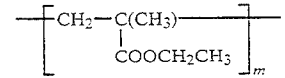

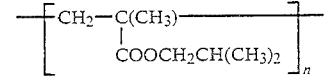

wherein $n/(m+n)$ is from 0.45 to 0.76. The denture base lining material according to the present invention is low in the rate of change in elastic strain, is less found in the sticky feeling, and can be readily peeled apart from the denture after the use.

7 Claims, No Drawings

DENTURE BASE LINING MATERIAL

FIELD OF THE INVENTION

The present invention relates to a tissue conditioner for denture-setting patients with deformation or inflammation in their oral mucosa, among denture base lining materials to be used in the dental remedy.

BACKGROUND OF THE INVENTION

During the use of a denture for a long period of time, the fitness becomes bad due to absorption of the alveolar ridge and the like, leading to reduction in its retention and stability. Furthermore, when an unfit denture is used, since a non-uniform stress is applied to a mucosa below the denture base, an ulcur and inflammation are likely generated, and a pain may be caused by the occlusal stress. For these reasons, it is necessary to prepare a new denture, or to rebase a denture in use to recover the fitness to the denture mucosa.

However, since the oral mucosa of a patient is in the unstable state for the reasons as described above, it is impossible to recover a good fitness unless these treatments are carried out after the oral mucosa has recovered a healthy state. The material to be used in such a case is a tissue conditioner. The tissue conditioner is laminated on the mucosal surface of a denture in use and used during a period of time of preparing a new denture or rebasing the denture in use.

Since this material is comprised of a powder and a liquid and when mixed, becomes a soft elastic material, if it is lined on the mucosal surface of a denture which has become unfit, the fitness of the denture is recovered so that the pain by the occlusal stress can be mitigated. If the pain is mitigated, the ulcur and inflammation in the oral mucosa disappear, leading to the change of the state of the oral mucosa with a lapse of time. For this reason, the tissue conditioner is provided with such properties that it deforms as the state of the oral mucosa changes. If such properties are not provided, the fitness of the denture is again lost so that the occlusal stress can not be uniformly borne by the entire mucosal surface. For this reason, the tissue conditioner is designed such that it readily generates creeps thereby automatically retain the fitness of the denture. As a material which can meet these requirements, a plastic material comprising a power component consisting of polyethyl methacrylate or a copolymer thereof and a liquid component cconsisting of a phthalic ester-based plasticizer containing about 8 to 20% by weight of ethanol has hitherto been used (see Norio HOSOI, *THE JOURNAL OF THE JAPAN DENTAL ASSOCIATION*, "Tissue conditioning of complete Denture Patients", Vol. 42, pp. 831-836, 1989).

As described above, these materials must have properties so as to readily generate creeps. For this reason, these materials likely become a material whose physical properties are extremely unstable and when mixed, become tacky so that they are difficult in handling. In addition, they involve the following defects during the use for one to two weeks.

(1) The elasticity is lost.
(2) Displeasing taste and stimulation when applied into the oral cavity.
(3) It is difficult to peel apart from the denture at the time when the tissue conditioner is exchanged.

These defects are considered to be caused by the matter that ethanol contained in the liquid component eluting in the oral cavity. however, if ethanol is excluded from the liquid component, the gelation time of the material greatly increases so that it can not be put into practical use.

SUMMARY OF THE INVENTION

In order to solve the problems of the tissue conditioner as described above, the present inventors have made extensive study. As a result, they have invented a denture base lining material according to the present invention.

The denture base lining material according to the present invention is used upon mixing a liquid component and a powder component, in which the liquid component comprises a phthalic ester-based plasticizer containing 5 to 15% by weight of ethyl alcohol and from 5 to 20% by weight of a liquid paraffin or squalane alone or a mixed solution thereof, and the powder component comprises a powder comsisting of any one of the following powders (a), (b), or (c), or a mixture of the two or more thereof:

(a) an ethyl methacrylate polymer powder containing from 1 to 5% by weight of a phthalic ester-based plasticizer;

(b) a copolymer powder represented by the following formula:

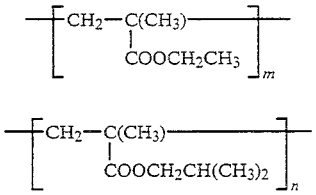

wherein $n/(m+n)$ is from 0.15 to 0.55, and containing from 0.5 to 2% by weight of a phthalic ester-based plasticizer; and (c) a mixed powder comprising a polyethyl methacrylate powder having a copolymer powder 30~75% by weight represented by the following formula mixed therewith:

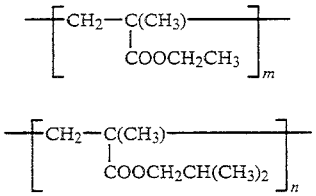

wherein $n/(m+n)$ is from 0.45 to 0.76.

DETAILED DESCRIPTION OF THE INVENTION

As described above, polyethyl methacrylate is mainly used in the powder component of the commercially available tissue conditioners (see Norio HOSOI, *THE JOURNAL OF THE JAPAN DENTAL ASSOCIATION*, "Tissue Conditioning of Complete Denture Patients", Vol. 42, pp. 831-836, 1989). Since the foregoing powders (a), (b), and (c) are more likely swollen by a phthalic ester than this polyethyl methacrylate, a dough-like material can be formed within a short period of time even if the content of ethanol in the liquid component is low. For this reason, the amount of ethanol eluted can be minimized so that the resulting tissue conditioner does not become hard in the oral cavity. Moreover, since the tissue conditioner according to the present invention is less tacky, not only the stickiness at the time of mixing can be reduced, but it can be easily removed off from the denture after the use.

The foregoing polymer powders (a), (b), and (c) can be obtained by previously mixing the monomer material with a phthalic ester and polymerizing them in the presence of an appropriate radical polymerization catalyst. While these polymer powders may be obtained by pulverization after obtaining a polymer by bulk polymerization, it is suitable to obtain them by suspension polymerization free from any need of pulverization. In the copolymers as described in the present invention, the polymerization ratios of the respective monomers are important, but it is of no importance whether the copolymers are a block copolymer or a random copolymer.

The content of isobutyl methacrylate and phthalic ester in the foregoing polymer powders (a), (b), and (c) is important.

Specifically, if the proportions of isobutyl methacrylate and the phthalic ester contained in the foregoing polymer powders (a), (b), and (c) are less than certain values, the gelation time greatly increases unless the amount of ethanol contained in the liquid is increased. Furthermore, the resulting tissue conditioner involves such a defect that it becomes hard in the oral cavity with a lapse of time like the conventional tissue conditioners using polyethyl methacrylate in the powder.

Contrary, if the proportions of isobutyl methacrylate and the phthalic ester contained in the foregoing polymer powders (a), (b), and (c) exceed certain values, the thermal stability of the polymer powder is lost, leading to a problem with respect to the storage stability. Specifically, when such a polymer powder is stored at 23° C. for a long period of time, not only the time required for the dough stage is delayed with a lapse of time, but as changes such as coagulation of the powder occur depending on the cases. Such changes must be avoided because when tissue conditioners are sold, they are possibly exposed to a high-temperature circumstance during distribution. For these reasons, there are a lower limit and an upper limit with respect to the proportions of isobutyl methacrylate and the phthalic ester contained in the foregoing polymer powders (a), (b), and (c). Specifically, the following proportions to the whole amount of the respective polymer powders must be met.

(1) in the case of the polymer powder (a), the proportion of the phthalic ester-based plasticizer must be from 1 to 5% by weight.

(2) In the case of the copolymer powder (b), the proportion of the phthalic ester-based plasticizer must be from 0.5 to 2% by weight, and the proportion of the isobutyl methacrylate must meet the following relation:

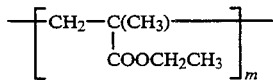

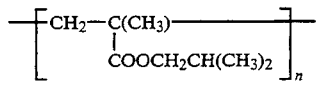

wherein n/(n+m) is from 0.15 to 0.55.

(3) In the case of the copolymer (c), the proportion of the isobutyl methacrylate must meet the following relation:

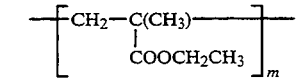

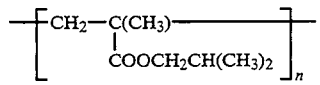

wherein n/(m+m) is from 0.45 to 0.76.

These proportions are realized by adjusting the compounding amounts of the respective components at the time of polymerization of the respective polymer powders.

The foregoing copolymer powder (c) is mixed with polyethyl methacrylate for use. As the mixing ratio of the copolymer powder (c) increases, the mixed powder more likely becomes in to the dough stage at the time of mixing with the liquid.

However, if the mixing ratio of the copolymer powder (c) exceeds 75% by weight, in the case that the mixed powder is stored for a long period of time, the time required for the dough stage is delayed with a lapse of time. Contrary, if the mixing ratio of the copolymer powder (c) is less than 30% by weight, the resulting tissue conditioner exhibits such a tendency that it becomes hard in the oral cavity with a lapse of time, whereby the characteristics of the tissue conditioner according to the present invention are lost.

Since the tissue conditioner is often exchanged during remedy, it is important that the tissue conditioner can be readily peeled apart from the denture. A liquid paraffin or squalane alone or a mixed solution thereof to be added to the liquid not only reduces the stickiness of the denture base lining material according to the present invention but decreases the adhesion strength of the tissue conditioner to the denture so that the tissue conditioner becomes easy to be peeled apart from the denture. In order to obtain definite effects, the addition amount of the liquid paraffin or squalane must be at least 4% by weight or more, and the effects increase with an increase of the addition amount. However, if the addition amount exceeds 20% by weight, there is given such a feeling that the oily matter oozes out on the surface of the tissue conditioner, thereby generates a sense of incongruity. Some additives which are expected to have the same effects as those of the liquid paraffin or squalane may be considered. For instance, while silicone oils are a typical separating material, almost all of silicone oils are not compatible with the liquid of the tissue conditioner so that they can not be used. In accordance with experiments done by the present inventors, certain silicone oils, such as polymethylphenyl siloxane, could be dissolved in the liquid of the tissue conditioner. however, the tissue conditioner prepared by kneading with this liquid involved such defects that not only the stickiness is not reduced, but the tensile strength of the material itself is lowered so that it is readily cut off when peeled apart the tissue conditioner from the denture. It may be considered to apply the liquid paraffin or squalane to the powder surface instead of adding it to the liquid. However, since the liquid paraffin or squalane slightly swells the powder, the storage stability is influenced. For this reason, it is proper to add the liquid paraffin or squalane to the liquid component.

As the powder component of the tissue conditioner according to the present invention, any one of the foregoing powders (a), (b), or (c), or a mixture of the two or more, thereof, is used. When the powder component is mixed with the liquid component comprising a phthalic ester-based plasticizer containing from 5 to 15% by weight of ethyl alcohol and from 5 to 20% by weight of a liquid paraffin or squalane alone or a mixed solution thereof, creep properties required as a tissue conditioner can be imparted. However, there may be a case in which more creep properties are required depending on the purpose of the remedy. In this case, this can be achieved by mixing the powder component of to 40% by weight or less of a copolymer powder represented by the following formula:

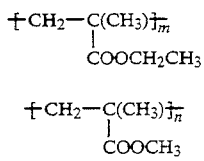

wherein $n/(m+n)$ is from 0.10 to 0.35.

While the creep properties increase with an increase of the addition amount thereof, the time required for the dough stage when mixed with the liquid is delayed. For this reason, the upper limit of the addition amount is 40% by weight, and if the addition amount exceeds this upper limit, the effect for reducing the amount of ethanol is lost due to the use of the polymer powders (a), (b), and (c) according to the present invention. Also, the creep properties increase with an increase of the amount of methyl methacrylate in the synthesis of the powder. However, if the molar amount of methyl methacrylate to be charged exceeds 35% of the whole, the obtained copolymer powder itself is hardly swollen by the liquid as described in the present invention. For this reason, a stringy stage appears at the time of mixing, and not only an unpleasant feeling is given, but the copolymer powder retains forever in the form of a hard powder in the dough-stage material, thereby impairs the fluidity of the tissue conditioner.

Contrary, if the molar amount of methyl methacrylate to be charged under 10% of the whole, the obtained copolymer powder is readily swollen by the liquid as described in the present invention, and the effect for increasing the creep properties is substantially lost.

A desired molecular weight of the polymer of the powder component according to the present invention is from 100,000 to 1,500,000. If the molecular weight of the polymer is under 100,000, the viscoelastic characteristic of the dough-stage material is so weak that the material is too hard. Furthermore, if the molecular weight of the polymer exceeds 1,500,000, the viscoelastic characteristic of the dough-stage material is so strong that the material is too soft, whereby the tissue conditioner does not play its role.

In addition, a desired grain size of the powder component according to the present invention is from 50 to 600 mesh. If the powder component has particles under 50-mesh and bigger grain diameter, when the tissue conditioner is built up in the mucosal surface side of the denture base and set up in the oral cavity, the flow between the denture base and the mucosal surface is bad. For this reason, not only it is impossible to properly adjust the mucosa, but a stimulation is followed. On the other hand, if the powder component has particles over 600-mesh, the flow between the denture base and the mucosal surface is good. However, the reaction between the powder component and the liquid component is so fast that the dough stage is initiated immediately after mixing and that there is left no room for operability. For this reason, the adjustment of the mucosa is not carried out smooth.

A desired viscosity of the liquid component according to the present invention is 1,000 cps or less. if the viscosity exceeds 1,000 cps, the compatibility with the powder component is markedly inhibited.

As the phthalic ester-based plasticizer used in the liquid component, any aliphatic hydrocarbon esters of phthalic acid can be preferably used. Suitable examples thereof include dibutyl phthalate, diheptyl phthalate, di-2-ethylhexyl phthalate, di-n-octyl phthalate, diisodecyl phthalate, butylbenzyl phthalate, diisononyl phthalate, ethylphthalylethyl glycolate and butylphthalylbutyl glycolate. However, while esters of a hydrocarbon having a lower number of carbon atoms, such as dimethyl phthalate and diethyl phthalate, can shorten the time required for the dough stage, as compared with other phthalic ester-based plasticizers, a stimulation is likely generated and such esters are preferably not used.

If the amount of ethanol to be added to the liquid is small, the time required for the dough stage is delayed. However, in the tissue conditioner according to the present invention, the same time required for the dough stage can be obtained even though the amount of ethanol to be added to the liquid is smaller than that in the commercially available tissue conditioners using polyethyl methacrylate in the powder, such as, for example, a trade mark "Soft Liner" (available from GC Corporation). However, if the amount of ethanol is under 5% by weight, the time required for the dough stage is too long by 20 minutes or longer. Contrary, if the addition amount exceeds 15% by weight, the time required for the dough stage is too short so that the operation is difficult.

EXAMPLES

The characteristic features as described above will be explained with reference to the following specific experimental examples. Various polymerizable monomers or mixed solutions of various polymerizable monomers and phthalic esters were each subjected to suspension polymerization in a gelatin aqueous solution, to prepare a plasticizer-containing polymer, the grain size of which was then adjusted by passing through a #250-mesh sieve. The thus obtained powder was mixed with a phthalic ester mixed solution containing ethanol and a liquid paraffin and then provided for the experiments.

Unless otherwise indicated, in each of Examples and Comparative Examples, the experiments were carried out under the common conditions as described below for the purpose of making the comparison easy.
(Common Conditions)

1. The liquid is used in an amount of 1.00 part by weight based on 1.22 parts by weight of the powder.
2. As the liquid component, dibutyl phthalate containing 10% by weight of ethanol and 10% by weight of a liquid paraffin is used.

Each of the experiments was carried out in the following way.

(1) Measurement of the time required for the dough stage: There is no definite standard with respect to the time required for the dough stage of the tissue conditioner. For this reason, the viscosity of the mixture at 23° C. was measured by means of an E-type viscometer with a lapse of time, and the time until after the initiation of mixing, the viscosity reached 1,500 Pa.sec was measured and taken as the time required for the dough stage. The number of revolution of the rotor was 1.0 r.p.m.

(2) Measurement of elastic strain, permanent strain, and rate of change in elastic strain:

There are no specific standards with respect to the evaluation of the softness and creep properties of the tissue conditioner. For this reason, the evaluation was carried out according to the test method for elastic strain and permanent strain of the dental alginate impression material as defined in JIS T6505. The elastic strain and permanent strain correspond to the creep size of the tissue conditioner, respectiviely. Specific measurement methods are as follows.

1. A mixed sample is poured into a silicone rubber mold having an inner diameter of 12.5 mm and a height of 20 mm, to prepare a dough-stage material.
2. The sample is stored in water at 37° C. for a prescribed period of time.
3. The sample is applied with a load by using an elastic strain tester as defined in JIS T6505.
4. A load of 0.01 MPa is first applied to read the dial gauge, the value of which is taken as "A".
5. Thirty seconds after the initiation of the experiment, a load is supplemented to make the total load to 0.05 MPa.
6. Sixty seconds after the initiation of the experiment, the dial gauge is read, the value of which is taken as "B". Immediately thereafter, the loads are removed.
7. Ninety seconds after the initiation of the experiment, a load of 0.01 MPa is again applied, and 102 seconds after the initiation of the experiment, the dial gauge is read, the value of which is taken as "C".
8. The elastic strain, permanent strain, and rate of change in elastic strain are calculated from the following equations.

Elastic Strain (%) = (A−B)/20 × 100
Permanent Strain (%) = (A−C)/20 × 100
Rate of change in Elastic Strain = elastic strain after one day/elastic strain after seven days (3) Storage Stability Test:
1. Each powder is stored at 23° C. for 3 months, and the change of time in the state of the dough is examined.
2. Each powder is stored at 45° C. for 2 weeks, and the change of time in the state of the dough is examined.

(1) Comparative Examples (a-1) to (a-3):

In order to make clear the characteristics of the tissue conditioners shown in the Examples, a commercially available tissue conditioner and a tissue conditioner comprising polyethyl methacrylate as a powder component were first provided for the tests.

Comparative Example (a-1)

Ethyl methacrylate was subjected to suspension polymerization in a gelatin aqueous solution, to prepare a polymer. The thus obtained powder was mixed with dibutyl phthalate containing 15% by weight of ethanol and 10% by weight of a liquid paraffin, and the mixture was provided for the tests.

Comparative Example (a-2)

Ethyl methacrylate was subjected to suspension polymerization in a gelatin aqueous solution, to prepare a polymer, which was then provided for the tests.

Comparative Example (a-3)

A powder of a commercially available tissue conditioner, trade mark "GC Soft Liner" (GC Corporation) was mixed with the liquid and then provided for the tests.

The results obtained are shown in Table 1. In any of the storage stability tests, the time required for the dough stage was not delayed, but the rate of change in elastic strain was so large as 1.45 to 1.50. In the commercially available tissue conditioner (a trade name "GC Soft Liner", manufacturing by GC Corporation) as shown in Comparative Example (a-3), the time required for the dough stage was 5.5 minutes. On the other hand, in the tissue conditioners using polyethyl methacrylate as a powder component as shown in Comparative Examples (a-1) and (a-2), in the case that the liquid contains 10% by weight of ethanol, the time required for the dough stage was so slow as 16.5 minutes, and in order to obtain the same time required for the dough stage as in "GC Soft Liner", the amount of ethanol should be increased to 15% by weight.

TABLE 1

| | Comparative Example No. | | |
|---|---|---|---|
| | (a-1) | (a-2) | (a-3) |
| Rate of change in elastic strain | 1.50 | 1.45 | 1.50 |
| Time required for the dough stage (min.) | | | |
| Before the storage | 5.4 | 16.5 | 5.5 |
| After the storage | 5.4 | 16.5 | 5.5 |
| Properties of powder after the storage at 45° C. | not Changed | not Changed | not Changed |

(2) Examples (b-1) to (b-3) and Comparative Examples (b-4) to (b-5):

Various tissue conditioners comprising plasticizer-containing polyethyl methacrylate as a powder component were prepared and then provided for the tests.

Example (b-1)

A mixed solution of 1% by weight of dibutyl phthalate and 99% by weight of ethyl methacrylate was subjected to suspension polymerization, to prepare a plasticizer-containing polymer, which was then provided for the tests.

Example (b-2)

A mixed solution of 3% by weight of dibutyl phthalate and 97% by weight of ethyl methacrylate was subjected to suspension polymerization, to prepare a plasticizer-containing polymer, which was then provided for the tests.

Example (b-3)

A mixed solution of 5% by weight of ethylphthalylethyl glycolate and 95% by weight of ethyl methacrylate was subjected to suspension polymerization, to prepare a plasticizer-containing polymer, which was then provided for the tests.

Comparative Example (b-4)

A mixed solution of 0.5% by weight of dibutyl phthalate and 99.5% by weight of ethyl methacrylate was subjected to suspension polymerization, to prepare a plasticizer-containing polymer, which was then provided for the tests.

Comparative Example (b-5)

A mixed solution of 7% by weight of dibutyl phthalate and 93% by weight of ethyl methacrylate was subjected to suspension polymerization, to prepare a plasticizer-containing polymer, which was then provided for the tests.

The results obtained are shown in Table 2. In any of the tissue conditioners as shown in Examples (b-1) to (b-3), the rate of change in elastic strain was 1.3 or less. These values were lower than those of the tissue conditioners using polyethyl methacrylate as a powder component as shown in Example 1 and commercially available tissue conditioners trade name "GC Soft Liner" (GC Corporation). In the tissue conditioner as shown in Comparative Example (b-5), while the rate of change in elastic strain was lower than those in the tissue conditioners as shown in Examples (b-1) to (b-3), not only the time required for the dough stage was delayed after the storage stability test, but the powder was coagulated after the storage stability test at 45° C. On the other hand, in the tissue conditioner as shown in Comparative Example (b-4), while the storage stability was good, the rate of change in elastic strain was large.

TABLE 2

|  | Example No. ||| Comparative Example No. ||
| --- | --- | --- | --- | --- | --- |
|  | (b-1) | (b-2) | (b-3) | (b-4) | (b-5) |
| Rate of change in elastic strain | 1.13 | 1.10 | 1.08 | 1.40 | 1.05 |
| Time required for the dough state (min.) |  |  |  |  |  |
| Before the storage | 10.0 | 8.5 | 7.1 | 15.9 | 5.1 |
| After the storage | 10.2 | 8.6 | 7.0 | 15.9 | 10.2 |
| Properties of powder after the storage at 45° C. | not changed | not changed | not changed | not changed | coagulated |

(3) Examples (c-1) to (c-6) and comparative Examples (c-7) to (c-10):

Various tissue conditioners comprising a plasticizer-containing ethyl methacrylate, isobutyl methacrylate copolymer as a powder component were prepared and then provided for the tests.

Example (c-1)

a mixed solution of 99.5% by weight of a liquid of a mixture of 0.15 mole of isobutyl methacrylate and 0.85 mole of ethyl methacrylate and 0.5% by weight of butylphthalylbutyl glycolate was subjected to suspension polymerization, to prepare a plasticizer-containing polymer, which was then provided for the tests.

Example (c-2)

A mixed solution of 99.5% by weight of a liquid of a mixture of 0.45 mole of isobutyl methacrylate and 0.55 mole of ethyl methacrylate and 0.5% by weight of butylphthalylbutyl glycolate was subjected to suspension polymerization, to prepare a plasticizer-containing polymer, which was then provided for the tests.

Example (c-3)

A mixed solution of 99.0% by weight of a liquid of a mixture of 0.45 mole of isobutyl methacrylate and 0.55 mole of ethyl methacrylate and 1.0% by weight of dibutyl phthalate was subjected to suspension polymerization, to prepare a plasticizer-containing polymer, which was then provided for the tests.

Example (c-4)

A mixed solution of 98.0% by weight of a liquid of a mixture of 0.45 mole of isobutyl methacrylate and 0.55 mole of ethyl methacrylate and 2.0% by weight of dibutyl phthalate was subjected to suspension polymerization, to prepare a plasticizer-containing polymer, which was then provided for the tests

Example (c-5)

A mixed solution of 99.0% by weight of a liquid of a mixture of 0.25 mole of isobutyl methacrylate and 0.75 mole of ethyl methacrylate and 1.0% by weight of dibutyl phthalate was subjected to suspension polymerization, to prepare a plasticizer-containing polymer, which was then provided for the tests.

Example (c-6)

A mixed solution of 99.0% by weight of a liquid of a mixture of 0.55 mole of isobutyl methacrylate and 0.45 mole of ethyl methacrylate and 1.0% by weight of dibutyl phthalate was subjected to suspension polymerization, to prepare a plasticizer-containing polymer, which was then provided for the tests.

Comparative Example (c-7)

A mixed solution of 99.7% by weight of a liquid of a mixture of 0.40 mole of isobutyl methacrylate and 0.60 mole of ethyl methacrylate and 0.3% by weight of butylphthalylbutyl glycolate was subjected to suspension polymerization, to prepare a plasticizer-containing polymer, which was then provided for the tests.

Comparative Example (c-8)

A mixed solution of 97.0% by weight of a liquid of a mixture of 0.15 mole of isobutyl methacrylate and 0.85 mole of ethyl methacrylate, and 3.0% by weight of dibutyl phthalate was subjected to suspension polymerization, to prepare a plasticizer-containing polymer, which was then provided for the tests.

Comparative Example (c-9)

A mixed solution of 99.0% by weight of a liquid of a mixture of 0.10 mole of isobutyl methacrylate and 0.90 mole of ethyl methacrylate and 1.0% by weight of dibutyl phthalate was subjected to suspension polymerization, to prepare a plasticizer-containing polymer, which was then provided for the tests.

Comparative Example (c-10)

A mixed solution of 99.0% by weight of a liquid of a mixture of 0.65 mole of isobutyl methacrylate and 0.35 mole of ethyl methacrylate and 1.0% by weight of dibutyl phthalate was subjected to suspension polymerization, to prepare a plasticizer-containing polymer, which was then provided for the tests.

The results obtained are shown in Table 3. In any of the tissue conditioners as shown in Examples (c-1) to (c-6), the rate of change in elastic strain was 1.3 or less. These values were lower than those of the tissue conditioners using polyethyl methacrylate as a powder component as shown in Examples and commercially available tissue conditioners trade name "GC Soft Liner" (GC Corporation). In the tissue conditioners as shown in Comparative Examples (c-8) and (c-10), while the rate of change in elastic strain was lower than those in the tissue conditioners as shown in Examples (c-1) to (c-6), not only the time required for the dough stage was delayed after the storage stability test, but the powder was coagulated after the storage stability test at 45° C. On the other hand, in the tissue conditioners as shown in Comparative Examples (c-7) and (c-9), while the storage stability was good, the rate of change in elastic strain was large.

Example (d-3)

A mixture of 75% by weight of a suspension polymerization product of a liquid of a mixture of 0.60 mole of isobutyl methacrylate and 0.40 mole of ethyl methacrylate, and 25% by weight of polyethyl methacrylate was used as a powder component and then provided for the tests.

Example (d-4)

A mixture of 50% by weight of a suspension polymerization product of a liquid of a mixture of 0.45 mole of isobutyl methacrylate and 0.55 mole of ethyl methacrylate, and 50% by weight of polyethyl methacrylate was used as a powder component and then provided for the tests.

Example (d-5)

A mixture of 50% by weight of a suspension polymerization product of a liquid of a mixture of 0.76 mole of isobutyl methacrylate and 0.24 mole of ethyl methacrylate, and 50% by weight of polyethyl methacrylate was used as a powder component and then provided for the tests.

Comparative Example (d-6)

A mixture of 20% by weight of a suspension polymerization product of a liquid of a mixture of 0.60 mole of

TABLE 3

| | Example No. | | | | | | Comparative Example No. | | | |
|---|---|---|---|---|---|---|---|---|---|---|
| | (c-1) | (c-2) | (c-3) | (c-4) | (c-5) | (c-6) | (c-7) | (c-8) | (c-9) | (c-10) |
| Rate of change in elastic strain | 1.30 | 1.25 | 1.21 | 1.19 | 1.25 | 1.19 | 1.40 | 1.18 | 1.40 | 1.03 |
| Time required for the dough stage (min.) | | | | | | | | | | |
| Before the storage | 9.9 | 9.5 | 9.1 | 8.4 | 9.8 | 6.8 | 15.3 | 9.1 | 14.3 | 5.5 |
| After the storage | 9.9 | 9.6 | 9.3 | 8.4 | 9.8 | 6.9 | 15.2 | 16.8 | 14.5 | 10.0 |
| Properties of powder after the storage at 45° C. | not changed | not changed | not changed | not changed | not changed | not changed | not changed | not coagulated | not changed | not coagulated |

(4) Examples (d-1) to (d-5) and Comparative Examples (d-6) to (d-9):

Various tissue conditioners comprising a mixture of an ethyl methacrylate, isobutyl methacrylate copolymer and polyethyl methacrylate as a powder component were prepared and then provided for the tests.

Example (d-1)

A mixture of 30% by weight of a suspension polymerization product of a liquid of a mixture of 0.60 mole of isobutyl methacrylate and 0.40 mole of ethyl methacrylate, and 70% by weight of polyethyl methacrylate was used as a powder component and then provided for the tests.

Example (d-2)

A mixture of 40% by weight of a suspension polymerization product of a liquid of a mixture of 0.65 mole of isobutyl methacrylate and 0.35 mole of ethyl methacrylate, and 60% by weight of polyethyl methacrylate was used as a powder component and then provided for the tests.

isobutyl methacrylate and 0.40 mole of ethyl methacrylate, and 80% by weight of polyethyl methacrylate was used as a powder component and then provided for the tests.

Comparative Example (d-7)

A mixture of 85% by weight of a suspension polymerization product of a liquid of a mixture of 0.60 mole of isobutyl methacrylate and 0.40 mole of ethyl methacrylate, and 15% by weight of polyethyl methacrylate was used as a powder component and then provided for the tests.

Comparative Example (d-8)

A mixture of 50% by weight of a suspension polymerization product of a liquid of a mixture of 0.30 mole of isobutyl methacrylate and 0.70 mole of ethyl methacrylate, and 50% by weight of polyethyl methacrylate was used as a powder component and then provided for the tests.

Comparative Example (d-9)

A mixture of 50% by weight of a suspension polymerization product of a liquid of a mixture of 0.90 mole of isobutyl methacrylate and 0.10 mole of ethyl methacrylate, and 50% by weight of polyethyl methacrylate was used as a powder component and then provided for the tests.

The results obtained are shown in Table 4. In any of the tissue conditioners as shown in Examples (d-1) to (d-5), the rate of change in elastic strain was 1.3 or less. These values were lower than those of the tissue conditioners using polyethyl methacrylate as a powder component as shown in Example 1 and commercially available tissue conditioners trade name "GC Soft Liner" (GC Corporation). In the tissue conditioners as shown in Comparative Examples (d-7) and (d-9), while the rate of change in elastic strain was lower than those in the tissue conditioners as shown in Examples (d-1) to (d-5), the time required for the dough stage was delayed after the storage stability test. On the other hand, in the tissue conditioners as shown in Comparative Examples (d-6) and (d-8), while the storage stability was good, not only the rate of change in elastic strain was large, but the time required for the dough stage was so slow as 15 minutes or longer.

In any of the powders, no coagulation occurred after the storage at 45° C.

Example (e-3)

A mixed solution of 99.0% by weight of a liquid of a mixture of 0.30 mole of isobutyl methacrylate and 0.70 mole of ethyl methacrylate, and 1.0% by weight of dibutyl phthalate was subjected to suspension polymerization, to prepare a plasticizer-containing polymer. A mixture of 60% by weight of this powder, 20% by weight of a suspension polymerization product of a liquid of a mixture of 0.50 mole of isobutyl methacrylate and 0.50 mole of ethyl methacrylate, and 20% by weight of polyethyl methacrylate was used as a powder component and then provided for the tests.

The results obtained are shown in Table 5. In any of the tissue conditioners as shown in Examples (e-1) to (e-3), the rate of change in elastic strain was 1.3 or less. These values were lower than those of the tissue conditioners using polyethyl methacrylate as a powder component and of the trade mark "GC Soft Liner" (GC Corporation). In these tissue conditioners, the time required for the dough stage was not delayed after the storage stability test.

TABLE 5

|  | Example No. | | |
| --- | --- | --- | --- |
|  | (e-1) | (e-2) | (e-3) |
| Rate of change in elastic strain | 1.10 | 1.20 | 1.15 |
| Time required for the dough stage (min.) | | | |
| Before the storage | 8.5 | 8.7 | 9.0 |
| After the storage | 8.7 | 8.7 | 9.0 |
| Properties of powder after the storage at 45° C. | not Changed | not Changed | not Changed |

TABLE 4

|  | Example No. | | | | | Comparative Example No. | | | |
| --- | --- | --- | --- | --- | --- | --- | --- | --- | --- |
|  | (d-1) | (d-2) | (d-3) | (d-4) | (d-5) | (d-6) | (d-7) | (d-8) | (d-9) |
| Rate of change in elastic strain | 1.25 | 1.20 | 1.25 | 1.28 | 1.28 | 1.43 | 1.20 | 1.40 | 1.10 |
| Time required for the dough state (min.) | | | | | | | | | |
| Before the storage | 9.0 | 8.0 | 8.5 | 9.5 | 9.9 | 15.1 | 9.2 | 13.2 | 7.5 |
| After the storage | 9.1 | 8.0 | 8.5 | 9.5 | 9.8 | 15.0 | 14.8 | 13.2 | 14.2 |
| Properties of powder after the storage at 45° C. | not changed | not changed | not changed | not changed | not changed | not changed | not changed | not changed | not changed |

Example (e-1)

A mixed solution of 5% by weight of dibutyl phthalate and 95% by weight of ethyl methacrylate was subjected to suspension polymerization, to prepare a plasticizer-containing polymer. A mixture of 50% by weight of this powder and 50% by weight of a plasticizer-containing polymer obtained by subjecting a mixed solution of 99.0% by weight a liquid of a mixture of 0.45 mole of isobutyl methacrylate, and 0.55 mole of ethyl methacrylate and 1.0% by weight of dibutyl phthalate to suspension polymerization was used as a powder component and then provided for the tests.

Example (e-2)

A mixed solution of 4% by weight of dibutyl phthalate and 96% by weight of ethyl methacrylate was subjected to suspension polymerization, to prepare a plasticizer-containing polymer. A mixture of 40% by weight of this powder, 30% by weight of a suspension polymerization product of a liquid of a mixture of 0.65 mole of isobutyl methacrylate and 0.35 mole of ethyl methacrylate, and 30% by weight of polyethyl methacrylate was used as a powder component and then provided for the tests.

(6) Examples (f-1) to (f-3) and Comparative Example (f-4):

Various tissue conditioners having a methyl methacrylate/ethyl methacrylate copolymer powder added to a powder component thereof were prepared and then provided for the tests.

40% by weight of a suspension polymerization product of a liquid of a mixture of 0.65 mole of isobutyl methacrylate and 0.35 mole of ethyl methacrylate was mixed with 60% by weight of polyethyl methacrylate, to prepare a powder (A). On the other hand, a liquid of a mixture of 0.20 mole of methyl methacrylate and 0.80 mole of ethyl methacrylate was subjected to suspension polymerization, to prepare a powder (B). The powder (A) was mixed with the powder (B) in different ratios and provided as a powder component for the tests.

The results obtained are shown in Table 6. The permanent strain could be increased with an increase of the amount of the powder (B) added. However, in Comparative Example (f-4) in which the powder (B) was added in an amount of 50% by weight, not only the time required for the dough stage was longer than those in Examples (f-1) to (f-3), but the rate of change in elastic strain was so large as 1.47.

TABLE 6

|  | Example No. | | | Comparative Example No. |
| --- | --- | --- | --- | --- |
|  | (f-1) | (f-2) | (f-3) | (f-4) |
| Weight ratio of compounded powder (A)/(B) | 100/0 | 90/10 | 70/30 | 50/50 |
| Permanent strain (%) (after 1 day in water at 37° C.) | 7.4 | 8.5 | 9.2 | 10.5 |
| Rate of change in elastic strain | 1.21 | 1.25 | 1.30 | 1.47 |
| Time required for the dough stage (min.) | | | | |
| Before the storage | 7.8 | 8.0 | 8.5 | 16.3 |
| After the storage | 7.9 | 8.0 | 8.6 | 16.3 |
| Properties of powder after the storage at 45° C. | not changed | not changed | not changed | not changed |

(7) Examples (g-1) to (g-3) and Comparative Example (g-4):

Various tissue conditioners having a methyl methacrylate/ethyl methacrylate copolymer powder (powder (D)) added to a powder component thereof were prepared and then provided for the tests.

A mixed solution of 3% by weight of dibutyl phthalate and 97% by weight of ethyl methacrylate was subjected to suspension polymerization, to prepare a powder (C). On the other hand, a liquid of a mixture of 0.10 mole of methyl methacrylate and 0.90 mole of ethyl methacrylate was subjected to suspension polymerization, to prepare a powder (D). The powder (C) was mixed with the powder (D) in a different ratio and provided as a powder component for the tests.

The results obtained are shown in Table 7. The permanent strain could be increased with an increase of the amount of the powder (D) added. However, in comparative Example (g-4) in which the powder (D) was added in an amount of 60% by weight, not only the time required for the dough stage was longer than those in Examples (g-1) to (g-3), but the rate of change in elastic strain was so large as 1.42.

TABLE 7

|  | Example No. | | | Comparative Example No. |
| --- | --- | --- | --- | --- |
|  | (g-1) | (g-2) | (g-3) | (g-4) |
| Weight ratio of compounded powder (C)/(D) | 100/0 | 80/20 | 60/40 | 40/60 |
| Permanent strain (%) (after 1 day in water at 37° C.) | 4.0 | 5.1 | 5.9 | 7.5 |
| Rate of change in elastic strain | 1.10 | 1.19 | 1.30 | 1.42 |
| Time required for the dough stage (min.) | | | | |
| Before the storage | 8.5 | 9.1 | 10.0 | 16.0 |
| After the storage | 8.6 | 9.1 | 9.9 | 16.3 |
| Properties of powder after the storage | not changed | not changed | not changed | not changed |

TABLE 7-continued

|  | Example No. | | | Comparative Example No. |
| --- | --- | --- | --- | --- |
|  | (g-1) | (g-2) | (g-3) | (g-4) |
| at 45° C. | | | | |

(8) Examples (h-1) to (h-3) and Comparative Example (h-4):

various tissue conditioners having a methyl methacrylate/ethyl methacrylate copolymer powder (powder (F)) added to a powder component thereof were prepared and then provided for the tests.

A mixed solution of 99.0% by weight of a liquid of a mixture of 0.45 mole of isobutyl methacrylate and 0.55 mole of ethyl methacrylate and 1.0% by weight of butylphthalylbutyl glycolate was subjected to suspension polymerization, to prepare a powder (E). On the other hand, a liquid of a mixture of 0.35 mole of methyl methacrylate and 0.65 mole of ethyl methacrylate was subjected to suspension polymerization, to prepare a powder (F). The powder (E) was mixed with the powder (F) in a different ratio and provided as a powder component for the tests.

The results obtained are shown in Table 8. The permanent strain could be increased with an increase of the amount of the powder F added. however, in Comparative Example (h-4) in which the powder F was added in amount of 50% by weight, not only the time required for the dough stage was longer than those in Examples (h-1) to (h-3), but the rate of change in elastic strain was so large as 1.42.

TABLE 8

|  | Example No. | | | Comparative Example No. |
| --- | --- | --- | --- | --- |
|  | (h-1) | (h-2) | (h-3) | (h-4) |
| Weight ratio of compounded powder (E)/(F) | 100/0 | 80/20 | 60/40 | 50/50 |
| Permanent strain (%) (after 1 day in water at 37° C.) | 4.5 | 5.5 | 6.2 | 8.0 |
| Rate of change in elastic strain | 1.21 | 1.25 | 1.30 | 1.42 |
| Time required for the dough stage (min.) | | | | |
| Before the storage | 9.1 | 9.5 | 9.9 | 16.3 |
| After the storage | 9.3 | 9.4 | 10.0 | 16.3 |
| Properties of powder after the storage at 45° C. | not changed | not changed | not changed | not changed |

(9) Comparative Example (i-1):

40% by weight of a suspension polymerization product of a liquid of a mixture of 0.60 mole of isobutyl methacrylate and 0.40 mole of ethyl methacrylate was mixed with 60% by weight of polyethyl methacrylate, to prepare a powder (G). On the other hand, a liquid of a mixture of 0.50 mole of methyl methacrylate and 0.50 mole of ethyl methacrylate was subjected to suspension polymerization, to prepare a powder (H). The powder (G) was mixed with the powder (H) in a weight ratio as described below and then provided as a powder component for the tests. The results obtained are shown in Table 9. While the tissue conditioner exhibited a high permanent strain, not only stringing occurred to generated stickiness at the time of mixing, but the time required for the dough stage was so long as 17 minutes.

TABLE 9

| | Comparative Example (i-1) |
|---|---|
| Weight ratio of compounded powder (G)/(H) | 70/30 |
| Permanent strain (%) (after 1 day in water at 37° C.) | 11.2 |
| Rate of change in elastic strain | 1.49 |
| Time required for the dough stage (min.) | |
| Before the storage | 17.0 |
| After the storage | 17.0 |
| Properties of powder after the storage at 45° C. | not changed |

(10) Examples (j-1) to (j-8) and comparative Examples (j-9) to (j-16):

Example (j-1)

A mixed solution of 5% by weight of dibutyl phthalate and 95% by weight of ethyl methacrylate was subjected to suspension polymerization, to prepare a plasticizer-containing polymer. This powder was mixed with an ethylphthalylethyl glycolate mixed solution containing 5% by weight of squalane and 6% by weight of ethanol and then provided for the tests.

Example (j-2)

A mixed solution of 5% by weight of dibutyl phthalate and 95% by weight of ethyl methacrylate was subjected to suspension polymerization, to prepare a plasticizer-containing polymer. This powder was mixed with an ethylphthalylethyl glycolate mixed solution containing 10% by weight of squalane and 6% by weight of ethanol and then provided for the tests.

Example (j-3)

A mixture of 30% by weight of a suspension polymerization product of a liquid of a mixture of 0.65 mole of isobutyl methacrylate and 0.35 mole of ethyl methacrylate, a mixture of 30% by weight of a suspension polymerization product of a liquid of a mixture of 0.22 mole of methyl methacrylate and 0.78 mole of ethyl methacrylate, and 40% by weight of polyethyl methacrylate was used as a powder component. This powder was mixed with a dibutyl phthalate mixed solution containing 5% by weight of a liquid paraffin and 10% by weight of ethanol and then provided for the tests.

Example (j-4)

A mixture of 30% by weight of a suspension polymerization product of a liquid of a mixture of 0.65 mole of isobutyl methacrylate and 0.35 mole of ethyl methacrylate, a mixture of 30% by weight of a suspension polymerization product of a liquid of a mixture of 0.22 mole of methyl methacrylate and 0.78 mole of ethyl methacrylate, and 40% by weight of polyethyl methacrylate was used as a powder component. This powder was mixed with a dibutyl phthalate mixed solution containing 10% by weight of a liquid paraffin and 10% by weight of ethanol and then provided for the tests.

Example (j-5)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. This powder was mixed with a dibutyl phthalate mixed solution containing 5% by weight of a liquid paraffin and 8% by weight of ethanol and then provided for the tests.

Example (j-6)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. This powder was mixed with a dibutyl phthalate mixed solution containing 15% by weight of a liquid paraffin and 8% by weight of ethanol and then provided for the tests.

Example (j-7)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. This powder was mixed with a dibutyl phthalate mixed solution containing 5% by weight of a liquid paraffin, 5% by weight of squalane, and 8% by weight of ethanol and then provided for the tests.

Example (j-8)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. this powder was mixed with a dibutyl phthalate mixed solution containing 10% by weight of a liquid paraffin, 5% by weight of squalane and 8% by weight of ethanol and then provided for the tests.

Comparative Example (i-9)

A mixed solution of 5% by weight of dibutyl phthalate and 95% by weight of ethyl methacrylate was subjected to suspension polymerization, to prepare a plasticizer-containing polymer. This powder was mixed with an ethylphthalylethyl glycolate mixed solution containing 0% by weight of squalane and 6% by weight of ethanol and then provided for the tests.

Comparative Example (j-10)

A mixed solution of 5% by weight of dibutyl phthalate and 95% by weight of ethyl methacrylate was subjected to suspension polymerization, to prepare a plasticizer-containing polymer. This powder was mixed with an ethylphthalylethyl glycolate mixed solution containing 25% by weight of squalane and 6% by weight of ethanol and then provided for the tests.

Comparative Example (j-11)

A mixture of 30% by weight of a suspension polymerization product of a liquid of 0.65 mole of isobutyl methacrylate and 0.35 mole of ethyl methacrylate, 30% by weight of a suspension polymerization product of a liquid of a mixture of 0.22 mole of methyl methacrylate and 0.78 mole of ethyl methacrylate, and 40% by weight of polyethyl methacrylate was used as a powder component. This powder was mixed with a dibutyl phthalate mixed solution containing 0% by weight of a liquid paraffin and 10% by weight of ethanol and then provided for the tests.

Comparative Example (j-12)

A mixture of 30% by weight of a suspension polymerization product of a liquid of a mixture of 0.65 mole of isobutyl methacrylate and 0.35 mole of ethyl methacrylate, 30% by weight of a suspension polymerization product of a liquid of a mixture of 0.22 mole of methyl methacrylate and 0.78 mole of ethyl methacrylate, and 40% by weight of polyethyl methacrylate was used as a powder component. This powder was mixed with a dibutyl phthalate mixed solution containing 25% by weight of a liquid paraffin and 10% by weight of ethanol and then provided for the tests.

Comparative Example (i-j-3)

A mixed solution of 99.0% by weight of a suspension polymerization product of a liquid of a mixture of 0.45 mole of isobutyl methacrylate and 0.55 mole of ethyl methacrylate and 1.0% by weight of dibutyl phthalate was subjected to suspension polymerization and used as a powder component. This powder was mixed with a dibutyl phthalate mixed solution containing 0% by weight of a liquid paraffin and 8% by weight of ethanol and then provided for the test.

Comparative Example (j-14)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. This powder was mixed with a dibutyl phthalate mixed solution containing 30% by weight of a liquid paraffin and 8% by weight of ethanol and then provided for the tests.

Comparative Example (j-15)

A mixed solution of 99.0% by weight of a suspension polymerization product of a liquid of a mixture of 0.45 mole of isobutyl methacrylate and 0.55 mole of ethyl methacrylate, and 1.0% by weight of dibutyl phthalate was subjected to suspension polymerization and used as a powder component. This powder was mixed with a dibutyl phthalate mixed solution containing 15% by weight of a liquid paraffin, 15% by weight of squalane, and 8% by weight of ethanol and then provided for the tests.

Comparative Example (j-16)

A commercially available tissue conditioner, "GC Soft Liner" (GC Corporation) was mixed and then provided for the tests.

If a liquid paraffin and/or squalane is added to the liquid, not only the stickiness of the tissue conditioner is reduced, but it is readily peeled apart from the denture after use. Thus, with respect to various tissue conditioners, the easiness in peeling apart from the denture was compared in the following manner.

Furthermore, the stickiness of the tissue conditioner was compared in terms of the sense of touch 15 minutes after the initiation of mixing.

Test Method for Evaluation of Easiness in Peeling Apart from Denture:

1. A denture cast is polymerized with a denture base material, trade mark "Aclon" (available from GC Corporation).
2. Various tissue conditioners are mixed and applied to the mucosal surface of a denture cast, to prepare samples.
3. After immersing each of the samples in water at 37° C. for one day and seven days, respectively, the tissue conditioner is peeled apart by hand, and the adhesive interface is observed.

The evaluation was carried out in accordance with the following criteria.
A: The tissue conditioner not left on the denture surface and could be peeled apart at the interface.
B: The tissue conditioner partly caused cohesive failure.
C: The tissue conditioner left on the denture surface and caused cohesive failure.

Also, the evaluation for the stickiness was carried out in accordance with the following criteria.
A: No stickiness caused.
B: Stickiness caused.

The results obtained are shown in Table 10. In the tissue conditioners having a liquid paraffin and/or squalane added to a liquid thereof as shown in Examples (j-1) to (j-8) and Comparative Examples (j-10), (j-12), (j-14), and (j-15), not only the stickiness was less found, but 7 days after immersing in water at 37° C., the tissue conditioner was well peeled apart from the denture. However, in Comparative Examples (j-10), (j-12), (j-14), and (j-15) in which a liquid paraffin and/or squalane is added in an amount exceeding 20% by weight, while the stickiness was not caused, the oil oozed out on the surface of the tissue conditioner so that an unpleasant feeling was imparted. In a commercially available tissue conditioner, trade mark "GC Soft Liner" (available from GC Corporation) as shown in Comparative Example (j-16), even one day after immersing in water at 37° C., it was difficult to peel apart it from the denture. In each of the tissue conditioners having no liquid paraffin or squalane added to a liquid thereof as shown in comparative Examples (j-9), (j-11), and (j-13), not only the stickiness was caused, but it was difficult to peel apart it from the denture.

TABLE 10

| State of adhesive interface | Example No. | | | | | | | |
|---|---|---|---|---|---|---|---|---|
| | (j-1) | (j-2) | (j-3) | (j-4) | (j-5) | (j-6) | (j-7) | (j-8) |
| After 1 day | A | A | A | A | A | A | A | A |
| After 7 days | A | A | A | A | A | A | A | A |
| Stickiness | A | A | A | A | A | A | A | A |
| State of adhesive interface | Comparative Example No. | | | | | | | |
| | (j-9) | (j-10) | (j-11) | (j-12) | (j-13) | (j-14) | (j-15) | (j-16) |
| After 1 day | C | A | C | A | C | A | A | C |

TABLE 10-continued

| After 7 days | C | A | C | A | C | A | A | C |
|---|---|---|---|---|---|---|---|---|
| Stickiness | C | A | C | A | C | A | A | C |

The tissue conditioner according to the present invention is less in the rate of change in elastic strain than the conventionally used tissue conditioners using polyethyl methacrylate as a powder. For this reason, since the tissue conditioner according to the present invention can retain the softness in the oral cavity for a long period of time, the effect as a tissue conditioner lasts long. In addition, in the tissue conditioner according to the present invetion, the sticky feeling which has been considered to be a problem in using a tissue conditioner is less so that it is easy to peel apart from a denture after the use. On the other hand, in the tissue conditioner according to the present invention, since it is possible to optionally set up the amount of permanent strain without impairing these advantages, tissue conditioners good for various applications can be obtained.

While the invention has been described in detail and with reference to specific embodiments thereof, it will be apparrent to one skilled in the art that various changes and modifications can be made therein without departing from the spirit and scope thereof.

What is claimed is:

1. A denture based lining material consisting essentially of a liquid component and a powder component, wherein:

the liquid component consists essentially of a mixture of an aliphatic hydrocarbon ester of phthalic acid, from 5 to 15% by weight of ethyl alcohol, and from 5 to 20% by weight of a material selected from the group consisting of liquid paraffin, squalane, and a mixed solution thereof, and wherein the powder component consists essentially of any one of the following powders (a), (b), or (c), or a mixture of two or more thereof:

(a) an ethyl methacrylate polymer powder containing from 1 to 5% by weight of an aliphatic hydrocarbon ester of phthalic acid plasticizer;

(b) a copolymer powder represented by the following formula:

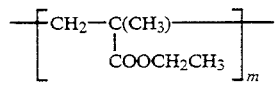

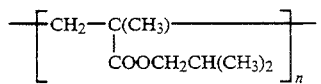

wherein n/(m+n) is from 0.15 to 0.55, and containing from 0.5 to 2% by weight of an aliphatic hydrocarbon ester of phthalic acid plasticizer; and (c) a mixed powder comprising a polyethyl methacrylate powder and 30 to 75% by weight of a copolymer powder represented by the following formula mixed therewith:

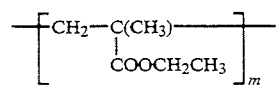

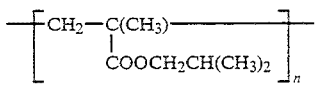

wherein n/(m+n) is from 0.45 to 0.76.

2. A denture base lining material as in claim 1, wherein the powder component has a grain size of from 50 mesh to 600 mesh.

3. A denture base lining material as in claims 1, wherein the viscosity of the liquid compoent is 1,000 cps or less.

4. A denture based lining material comprising a liquid component and a powder component, wherein:

the liquid component comprises a mixture of a phthalic ester plasticizer, from 5 to 15% by weight of ethyl alcohol, and from 5 to 20% by weight of a material selected from the group consisting of liquid paraffin, squalane, and a mixed solution thereof, and wherein the powder component comprises of any one of the following powders (a), (b), or (c), or a mixture of two or more thereof:

(a) an ethyl methacrylate polymer powder containing from 1 to 5% by weight of a phthalic ester plasticizer;

(b) a copolymer powder represented by the following formula:

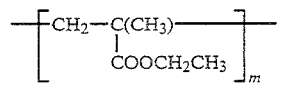

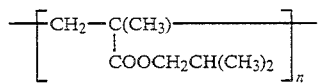

wherein n/(m+n) is from 0.15 to 0.55, and containing from 0.5 to 2% by weight of a phthalic ester plasticizer; and (c) a mixed powder comprising a polyethyl methacrylate powder and 30 to 75% by weight of a copolymer powder represented by the following formula mixed therewith:

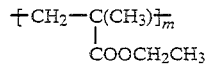

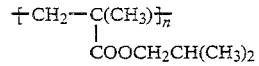

wherein n/(m+n) is from 0.45 to 0.76;

said powder component further comprising up to 40% by weight of the following copolymer powder:

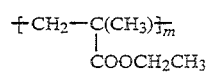

-continued

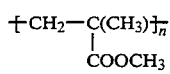

wherein n/(n+m) is from 0.10 to 0.35.

5. The denture based lining material as claimed in claim 4, wherein the copolymer powder having the formula:

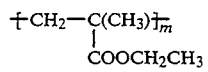

-continued

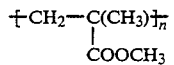

is present in an amount sufficient to affect the creep properties of the denture based lining material, as compared with the creep properties of a denture based lining material according to claim 4 which does not comprise the copolymer powder having the formula depicted above.

6. The denture based lining material as claimed in claim 1, wherein said powder component consists essentially of powder (b), powder (c), or a mixture thereof.

7. The denture based lining material as claimed in claim 3, wherein the liquid component has a viscosity of 1,000 cps or less.

* * * * *